(12) United States Patent
Walker

(10) Patent No.: US 9,023,111 B2
(45) Date of Patent: May 5, 2015

(54) TOTAL KNEE REPLACEMENT SUBSTITUTING FUNCTION OF ANTERIOR CRUCIATE LIGAMENT

(71) Applicant: Peter Stanley Walker, New York, NY (US)

(72) Inventor: Peter Stanley Walker, New York, NY (US)

(73) Assignee: New York University, New York, NY (US)

( * ) Notice: Subject to any disclaimer, the term of this patent is extended or adjusted under 35 U.S.C. 154(b) by 115 days.

(21) Appl. No.: 13/955,312

(22) Filed: Jul. 31, 2013

(65) Prior Publication Data

US 2014/0046452 A1 Feb. 13, 2014

Related U.S. Application Data

(60) Provisional application No. 61/681,465, filed on Aug. 9, 2012.

(51) Int. Cl.
*A61F 2/38* (2006.01)
*A61F 2/30* (2006.01)

(52) U.S. Cl.
CPC .................. *A61F 2/3886* (2013.01); *A61F 2/38* (2013.01); *A61F 2002/30934* (2013.01); *A61F 2/3859* (2013.01); *A61F 2/389* (2013.01); *A61F 2002/30935* (2013.01)

(58) Field of Classification Search
CPC ... A61F 2/3868; A61F 2/3886; A61F 2/3859; A61F 2/389; A61F 2/38; A61F 2002/30935; A61F 2002/30934

USPC .......... 623/20.14, 20.15, 20.26–20.31, 20.33
See application file for complete search history.

(56) References Cited

U.S. PATENT DOCUMENTS

| | | | |
|---|---|---|---|
| 4,959,071 A * | 9/1990 | Brown et al. | 623/20.27 |
| 5,282,869 A * | 2/1994 | Miyajima et al. | 623/20.27 |
| 5,549,688 A * | 8/1996 | Ries et al. | 623/20.35 |
| 5,725,584 A * | 3/1998 | Walker et al. | 623/20.29 |
| 5,989,261 A * | 11/1999 | Walker et al. | 606/102 |
| 6,264,697 B1 * | 7/2001 | Walker | 623/20.27 |
| 6,458,160 B2 * | 10/2002 | Biegun et al. | 623/20.27 |
| 6,582,469 B1 * | 6/2003 | Tornier | 623/20.27 |
| 6,699,291 B1 * | 3/2004 | Augoyard et al. | 623/20.27 |
| 6,770,099 B2 * | 8/2004 | Andriacchi et al. | 623/20.35 |
| 7,465,320 B1 * | 12/2008 | Kito et al. | 623/20.27 |
| 7,922,770 B2 * | 4/2011 | Tsakonas | 623/20.27 |
| 7,955,394 B2 * | 6/2011 | Hotokebuchi et al. | 623/20.14 |
| 8,137,407 B2 * | 3/2012 | Todd et al. | 623/20.33 |
| 8,211,181 B2 * | 7/2012 | Walker | 623/20.21 |
| 8,292,964 B2 * | 10/2012 | Walker | 623/20.21 |
| 8,292,965 B2 * | 10/2012 | Walker | 623/20.27 |
| 8,298,288 B2 * | 10/2012 | Walker | 623/20.21 |
| 8,382,845 B2 * | 2/2013 | Metzger et al. | 623/20.21 |
| 8,545,571 B2 * | 10/2013 | Collazo et al. | 623/20.27 |
| 8,808,387 B2 * | 8/2014 | Hawkins et al. | 623/20.27 |
| 2004/0054417 A1 * | 3/2004 | Soffiati et al. | 623/20.31 |
| 2007/0135925 A1 * | 6/2007 | Walker | 623/20.21 |

(Continued)

FOREIGN PATENT DOCUMENTS

WO    PCT/US13/052890    11/2013

*Primary Examiner* — Alvin Stewart
(74) *Attorney, Agent, or Firm* — Kelley, Drye & Warren LLP

(57) ABSTRACT

A total knee replacement prosthesis comprising condylar and intercondylar bearing surfaces configured to manage anterior/posterior displacement between the articulating femoral and tibial components.

9 Claims, 2 Drawing Sheets

(56) References Cited

U.S. PATENT DOCUMENTS

| | | | |
|---|---|---|---|
| 2007/0135926 A1* | 6/2007 | Walker | 623/20.31 |
| 2009/0043395 A1* | 2/2009 | Hotokebuchi et al. | 623/20.29 |
| 2009/0204221 A1* | 8/2009 | Walker | 623/20.27 |
| 2009/0319047 A1* | 12/2009 | Walker | 623/20.15 |
| 2009/0319048 A1* | 12/2009 | Shah et al. | 623/20.29 |
| 2010/0191341 A1* | 7/2010 | Byrd | 623/20.3 |
| 2012/0029649 A1* | 2/2012 | Collazo et al. | 623/20.28 |
| 2012/0095563 A1* | 4/2012 | Sanford et al. | 623/20.27 |
| 2012/0203350 A1* | 8/2012 | Hagen et al. | 623/20.22 |
| 2013/0190884 A1* | 7/2013 | Hashida | 623/20.29 |
| 2013/0197654 A1* | 8/2013 | Samuelson et al. | 623/20.35 |
| 2013/0204382 A1* | 8/2013 | Walker | 623/20.31 |
| 2013/0297032 A1* | 11/2013 | Li et al. | 623/20.35 |
| 2014/0046452 A1* | 2/2014 | Walker | 623/20.27 |

\* cited by examiner

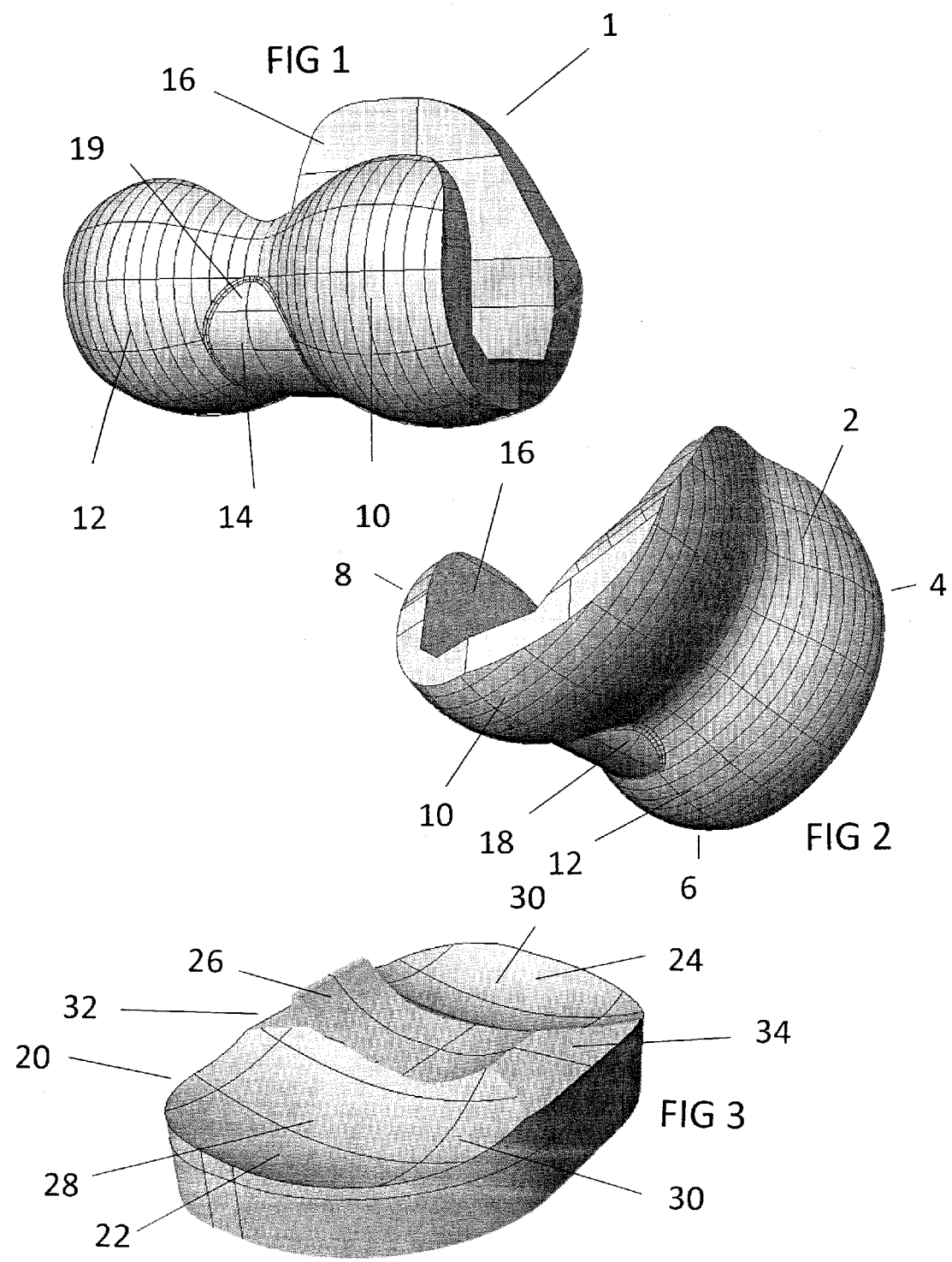

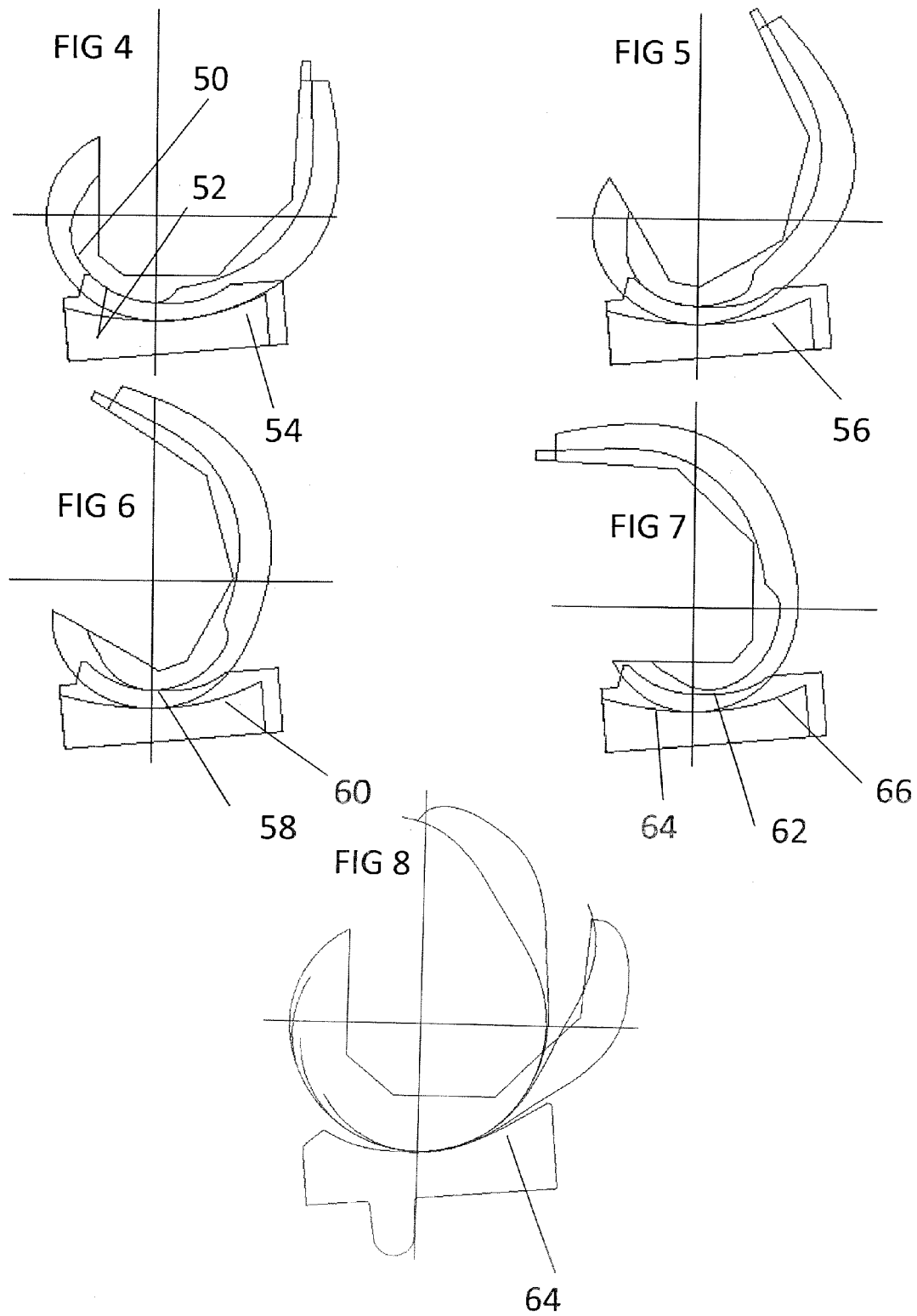

TOTAL KNEE REPLACEMENT SUBSTITUTING FUNCTION OF ANTERIOR CRUCIATE LIGAMENT

PRIORITY CLAIM TO PREVIOUS PATENT APPLICATION

This U.S. utility patent application claims the benefit of U.S. Provisional Patent Application No. 61/681,465 that was filed on Aug. 9, 2012, the entire disclosure of which is incorporated by reference in its entirety. All references cited in this specification, and their references, are incorporated by reference herein where appropriate for teachings of additional or alternative details, features, and/or technical background.

BACKGROUND OF THE INVENTION

1. Field of the Invention

The present invention generally relates to prosthetic knee where the femoral and tibial components comprise condylar and intercondylar bearing surfaces that provide management of anterior-posterior displacement throughout the full flexure range.

2. Description of the Related Art

The first condylar replacement type of total knee replacement intended for cruciate resection was the Freeman-Swanson (Freeman, Swanson, Todd 1977), designed in the late 1960's. This used a roller-in-trough geometry to provide stability and a large area of contact to minimize the wear. Also in the late 1960's, Gunston (1971) designed a conservative total knee consisting of independent runners embedded in the femoral and tibial condyles. In the early 1970's, Seedhom (1974) designed a total knee based on anatomical knee specimens, where he directly replicated the femoral surfaces and the tibial surfaces with the menisci present. A similar concept was described by Ewald in a patent. The Total Condylar knee was designed in the early 1970's with partially conforming bearing surfaces in the frontal and sagittal planes In order to provide an appropriate combination of laxity and stability (Walker, Wang, Masse 1974; Insall, Ranawat, Scott, Walker 1976). The relative radii were calculated to provide similar mechanical characteristics to that of the anatomic knee. The Kinematic Stabilizer and Insall-Burstein designs added an intercondylar cam-post mechanism to prevent anterior femoral subluxation and posterior femoral displacement in high flexion (Walker & Sathasivam, 2000; Robinson RD 2005). Posterior femoral displacement in flexion was achieved by added on intercondylar cam-post mechanism to prevent anterior femoral subluxation and provide posterior femoral displacement in high flexion. Since then, these 'posterior stabilized' (PS) designs have been modified and refined, and are now in widespread use. Typically the sagittal and frontal geometrics are defined by connecting radii generally resembling the Total Condylar, while the intercondylar cam-post is designed separately, usually contacting from mid-flexion to maximum flexion. In such designs, the lateral and medial condyles are often symmetric, providing no lateral or medial bias to the motion. While symmetric designs can use simply derived geometry for both the femoral and tibial surfaces, as well as for cams and posts, such an approach is more difficult if anatomic motion patterns are required. For any type of design where both of the cruciates are resected, the problem of replicating the constraints provided by these ligaments remains a challenge to this day. In particular, providing AP stability and rotational laxity throughout flexion, while inducing femoral rollback to achieve high flexion angles without posterior impingement, seems difficult to achieve with the bearing surfaces alone, even with a cam-post mechanism.

More recently, designs have been produced which provide greater medial than lateral constraint. One design concept, the medial pivot, uses a ball-in-a-socket for the medial compartment, and surfaces of low constraint on the lateral side (Blaha 2004; Moonot, 2009). Another design, the Journey Knee (Reis, Victor, Bellemans 2006, Victor Bellemans 2006), has a more constrained medial side and a cam-pivot which results in more posterior femoral displacement laterally. These designs are intended to achieve more normal kinematics, a goal that is receiving more attention today in an effort to improve function, especially in more active patients. So far however, these designs do not replicate anatomic motion and laxity-stability characteristics, or have certain motion abnormalities in some patients. Hence there is still a need for a design that will allow close restoration of normal kinematics, and provides reliability and reproducibility.

BRIEF SUMMARY OF THE INVENTION

In embodiments a condylar replacement total knee is disclosed which has partially conforming femoral and tibial condylar bearing surfaces which carry the load across the knee joint, and intercondylar guiding surfaces on both the femoral and tibial components. The intercondylar guiding surfaces are shaped to substitute for the function of the anterior cruciate ligament, notably by limiting the posterior displacement of the femur on the tibia in the first half of the flexion range. Over the second half of the flexion range, the femur is allowed to displace posteriorly on the tibia resulting from the partial conformity between the above-mentioned femoral and tibial condylar bearing surfaces. The function of this basic design can be enhanced by several other features. Prevention of excessive anterior displacement of the femur on the tibia over the first half of the flexion range is provided by making the distal-anterior sagittal curve of the medial femoral condyle steep, corresponding with a steep bearing surface on the apposing anterior tibial condylar surface. Posterior displacement of the femur on the tibia in the second half of flexion is induced by making the lowest points on the tibial condylar bearing surfaces towards the posterior of the tibia in combination with shallow surfaces. Provision for internal-external rotation of the femur on the tibia without edge contacts is made by rounding of the intercondylar guide surfaces. Reduced anterior-posterior displacement on the medial side and increased anterior-posterior displacement on the lateral side is provided by increased dishing of the medial tibial condylar bearing surface and less dishing of the lateral tibial condylar bearing surface.

In embodiments there is presented a total knee prosthesis comprising: a femoral component comprising a femoral intercondylar bearing surface positioned between a lateral femoral condylar surface and a medial femoral condylar surface, said intercondylar bearing surface extending from an approximately distal location to a posterior location and having a sagittal radius smaller than that of said lateral and medial femoral condylar bearing surfaces, but with a center of curvature close to a center of curvature of said lateral and medial femoral condylar surfaces; a tibial component in articulating contact with said femoral component comprising a tibial intercondylar bearing surface positioned between a lateral tibial condylar surface and a medial tibial condylar surface, said tibial intercondylar surfaces are concave with minimum surface elevation points located posteriorly with respect to the middle of said tibial component; wherein, for flexion angles of approximately 0 (zero) degrees, portions of said femoral intercondylar bearing surfaces and said a tibial intercondylar bearing surfaces are conformal and are configured to prevent posterior displacement of the femoral component with respect to the tibial component and portions of said femoral condylar surfaces and said tibial condylar surfaces are conformal and are configured to prevent anterior displacement of the femoral component; and, for flexion angles of approximately 30 degrees, a portion of said femoral intercondylar bearing surface and said tibial intercondylar bearing surface are conformal and are configured to prevent posterior displacement of the femoral component and portions of said femoral condylar surfaces and said tibial condylar surfaces are partially conformal and are configured to allow anterior displacement of the femoral component; and, for flexion angles of approximately 60 degrees, there is partial conformity between said femoral intercondylar bearing surface and said a tibial intercondylar bearing surface; and, for flexion angles of approximately 90 degrees, said femoral intercondylar bearing surface and said tibial intercondylar bearing surfaces are configured so that there is no contact.

DESCRIPTION OF THE FIGURES

The accompanying figures incorporated in and forming a part of the specification illustrate several aspects of embodiments of the invention and, together with the description, serve to explain the embodiments.

FIG. 1 is a posterior-lateral view of the femoral component.

FIG. 2 is an anterior-medial view of the femoral component.

FIG. 3 is an anterior-medial view of the tibial component.

FIG. 4 is a sagittal section through the center of the femoral and tibial components showing the intercondylar bearing surfaces, and through the center of the lateral femoral and tibial condyles, with the knee at 0 degrees flexion.

FIG. 5 is a sagittal section through the center of the femoral and tibial components showing the intercondylar bearing surfaces, and through the center of the lateral femoral and tibial condyles, with the knee at 30 degrees flexion.

FIG. 6 is a sagittal section through the center of the femoral and tibial components showing the intercondylar bearing surfaces, and through the center of the lateral femoral and tibial condyles, with the knee at 60 degrees flexion.

FIG. 7 is a sagittal section through the center of the femoral and tibial components showing the intercondylar bearing surfaces, and through the center of the lateral femoral and tibial condyles, with the knee at 90 degrees flexion.

FIG. 8 is a sagittal section through the center of the medial femoral and tibial condyles, showing the tibial condyle at 0 degrees flexion, and the femoral condyle at 0, 30, 60 and 90 degrees flexion.

DETAILED DESCRIPTION OF EMBODIMENTS OF THE INVENTION

In an embodiment, as shown in FIGS. 1, 2, and 3, the femoral component 1 comprises an anterior portion 2, a distal portion 6, and a posterior portion 8. The anterior portion 2 is called the patella flange 4 along which the patella (not shown) slides during flexion-extension. The lateral femoral condyle 12 and the medial femoral condyle 10 are biconvex surfaces which locate against their corresponding tibial condylar bearing surfaces 24 and 22. The interior surface of the femoral component 16 comprises facets that are typically used to interface against the prepared surface of the distal femur. A femoral intercondylar bearing surface 14 is located between the femoral condyles 10 and 12 and extends from a distal location 18 to a posterior location 19. The outer radius of the femoral intercondylar bearing surface seen in the sagittal view, from the lateral or medial sides, is smaller than that of the lateral 12 and medial 10 femoral condyles. The distal region of the intercondylar bearing surface 18 is configured to not impinge on the patella even in high flexion.

The tibial component 20 comprises a medial condylar bearing surface 22, a lateral condylar bearing surface 24, and a tibial intercondylar bearing surface 26. In describing the interaction between the femoral and tibial condylar and intercondylar surfaces, we define conformity in a plane as meaning the femoral and tibial radii are the same, preventing shear motion between the femur and the tibia. It will be appreciated that there is effectively conformity if the radii are very close together rather than being exactly the same. Partial conformity means that there is a difference in the radii, allowing some shear motion to occur but where the motion is limited. It will be appreciated that the shear motion will be larger, the larger the difference in the radii. The condylar bearing surfaces 22 and 24 are biconcave surfaces, onto which the femoral condyles 10 and 12 locate. The portions of the radii of the tibial condylar bearing surfaces in the sagittal plane and in the coronal plane are the same as or larger than the corresponding portions of the radii of the femoral condyles 10 and 12. The sagittal radius of the tibial intercondylar bearing surface 26 is the same or larger than that of the femoral intercondylar bearing surface 14. The tibial intercondylar bearing surface and the femoral intercondylar bearing surface are configured so that they are in conformity up to about the mid-range of flexion. The lowest points on the femoral condylar bearing surfaces 10 and 12 generally contact with the lowest points on the tibial condylar bearing surfaces 28 and 30. In one embodiment, points 28 and 30, the lowest points of the tibial condylar bearing surfaces, are located posteriorly of the mid-point of the tibial component. The intercondylar bearing surfaces are conforming or partially conforming so that over the range from extension to mid-range of flexion, the femur is prevented from displacing posteriorly on the tibia. As flexion increases beyond mid-range, however, it is preferable that some posterior displacement of the femur occur in order to increase the range of flexion. If the lowest points on the tibial condylar surfaces are positioned posterior of the mid-point, for example between 10-20 mm from the posterior, then the femoral condyles will preferably displace posteriorly to locate in these lowest points due to gravity forces. This is accomplished by the intercondylar bearing surfaces having no conformity or losing contact altogether. To produce a still more anatomic behavior, the lowest point on the lateral tibial condylar surface can be closer to the posterior of the tibial component than the lowest point on the medial tibial condylar surface.

Further improvement in anatomic-like function may be achieved by reducing the anterior sliding of the medial femoral condyle on the tibia, especially in early flexion. This can be accomplished by increasing the steepness of the distal-anterior surface of both the medial femoral condyle 10 and the corresponding area of the tibia 30. A further feature to produce more anatomic function is to increase the conformity on the medial side and reduce the conformity on the lateral side. This can be accomplished by a reduction in the sagittal radius of the medial tibia 22, and increase the sagittal radius of the lateral tibia 24. It will be understood that these geometrical changes can be accomplished by making changes in either or both of the femoral and tibial condylar surfaces.

FIG. 4 portrays a section taken in the sagittal plane through the femoral and tibial component, at 0 degrees of flexion. The femoral intercondylar bearing surface 50 and the tibial intercondylar bearing surface 52 are in close conformity, preventing posterior displacement of the femoral component on the tibial component. The anterior sliding of the femur on the tibia is restricted by the close conformity between the distal-anterior femoral and tibial condylar bearing surfaces 54. In FIG. 5, at 30 degrees flexion, the femoral and tibial intercondylar surfaces are still in close conformity, preventing posterior displacement of the femur on the tibia. However there is now partial conformity between the distal-anterior femoral and tibial condylar bearing surfaces 56, which would allow some anterior displacement of the femur on the tibia. In FIG. 6, at 60 degrees flexion, there is partial conformity between the femoral and tibial intercondylar bearing surfaces 58, allowing some posterior displacement of the femur on the tibia. Again, distal-anterior there is partial femoral-tibial condylar surface conformity 60. In FIG. 7, by 90 degrees flexion, there is no interaction between the intercondylar bearing surfaces 62, allowing posterior displacement of the femur on the tibia. However if the lowest points of the lateral and medial tibial condylar bearing surfaces are more posterior such as at location 64, it would induce the femur to move posterior so that the lowest points on the femoral condyles will located at the lowest points on the tibial condylar surface 64. The location of the lowest point on the tibial condylar surface can be chosen more posterior on the lateral side compared with medial side, to induce more posterior lateral displacement than medial, thus producing an axial rotation of the femur on the tibia. Also, as at 30 and 60 degrees flexion, there is partial femoral tibial conformity distal anterior 66. The amount of anterior displacement of the femur on the tibia can be reduced by making the femoral and tibial surfaces steeper at points 56, 60, and 66.

STATEMENT REGARDING PREFERRED EMBODIMENTS

While the invention has been described with respect to preferred embodiments, those skilled in the art will readily appreciate that various changes and/or modifications can be made to the invention without departing from the spirit or scope of the invention as defined by the appended claims. All documents cited herein are incorporated by reference herein where appropriate for teachings of additional or alternative details, features and/or technical background.

What is claimed:

1. A total knee prosthesis comprising:
a femoral component comprising a femoral intercondylar bearing surface positioned between a lateral femoral condylar surface and a medial femoral condylar surface, said intercondylar bearing surface extending from an approximately distal location to a posterior location and having a sagittal radius smaller than that of said lateral and medial femoral condylar bearing surfaces, but with a center of curvature close to a center of curvature of said lateral and medial femoral condylar surfaces;
a tibial component in articulating contact with said femoral component comprising a tibial intercondylar bearing surface positioned between a lateral tibial condylar surface and a medial tibial condylar surface, said tibial intercondylar surfaces are concave with minimum surface elevation points located posteriorly with respect to a middle of said tibial component;
wherein, for flexion angles of approximately 0 (zero) degrees, portions of said femoral intercondylar bearing surfaces and said tibial intercondylar bearing surfaces are conformal and are configured to prevent posterior displacement of the femoral component with respect to the tibial component and portions of said femoral condylar surfaces and said tibial condylar surfaces are conformal and are configured to prevent anterior displacement of the femoral component;
and, for flexion angles of approximately 30 degrees, a portion of said femoral intercondylar bearing surface and said a tibial intercondylar bearing surface are conformal and are configured to prevent posterior displacement of the femoral component and portions of said femoral condylar surfaces and said tibial condylar surfaces are partially conforming;
and, for flexion angles of approximately 60 degrees, there is partial conformity between said femoral intercondylar bearing surface and said tibial intercondylar bearing surface;
and, for flexion angles of approximately 90 degrees, said femoral intercondylar bearing surface and said tibial intercondylar bearing surfaces are configured so that there is no contact.

2. A total knee prosthesis in accordance with claim 1 where the sagittal radius of the femoral and tibial intercondylar surfaces are 3-6 mm less that the radius of the lateral and medial bearing surfaces from the distal end of the femur to the posterior.

3. A total knee prosthesis in accordance with claim 1 where the tibial intercondylar surfaces interact in the range of approximately 0 to 60 degrees of flexion.

4. A total knee prosthesis in accordance with claim 1 where the sagittal radius of the tibial intercondylar surface is 0-5 mm larger than that of the femoral intercondylar surface.

5. A total knee prosthesis in accordance with claim 1 where the centers of the intercondylar bearing surfaces can deviate from the centers of the condylar bearing surfaces at equivalent angles by 0-5 mm.

6. A total knee prosthesis in accordance with claim 1 where the distal-anterior surface of the medial femoral condyle is made steeper in the sagittal view, together with a corresponding increase in steepness of the apposing anterior tibial bearing surface.

7. A total knee prosthesis in accordance with claim 1 where the lowest points on the lateral and medial tibial bearing surfaces are between 10-20 mm from the posterior of the tibial component.

8. A total knee prosthesis in accordance with claim 7 where the lowest point on the lateral tibial condyle is further posterior than on the medial tibial condyle.

9. A total knee prosthesis in accordance with claim 1 where the sagittal radius of the medial tibial condyle is less than that of the lateral tibial condyle.

\* \* \* \* \*